United States Patent
Teunissen

(10) Patent No.: US 6,652,823 B2
(45) Date of Patent: Nov. 25, 2003

(54) PROCESS FOR THE SYNTHESIS OF VPO CATALYSTS

(75) Inventor: Herman Teunissen, Hillerod (DK)

(73) Assignee: Haldor Topsoe A/S, Lyngby (DK)

( * ) Notice: Subject to any disclaimer, the term of this patent is extended or adjusted under 35 U.S.C. 154(b) by 22 days.

(21) Appl. No.: 09/735,801

(22) Filed: Dec. 14, 2000

(65) Prior Publication Data

US 2002/0115562 A1 Aug. 22, 2002

Related U.S. Application Data

(60) Provisional application No. 60/171,455, filed on Dec. 22, 1999.

(51) Int. Cl.[7] .............................................. C01B 25/37
(52) U.S. Cl. ...................... 423/308; 423/309; 423/311; 502/209; 549/262
(58) Field of Search ................................ 423/308, 309, 423/311; 502/209

(56) References Cited

U.S. PATENT DOCUMENTS

| | | | | |
|---|---|---|---|---|
| 4,016,105 A | | 4/1977 | Kerr | |
| 4,147,661 A | * | 4/1979 | Higgins | 502/209 |
| 4,209,423 A | | 6/1980 | Hutchings et al. | |
| 4,569,925 A | | 2/1986 | Yang et al. | |
| 4,604,371 A | * | 8/1986 | Moorehead | 502/209 |
| 5,364,824 A | * | 11/1994 | Andrews et al. | 502/209 |
| 6,261,988 B1 | * | 7/2001 | Matsuura | 502/209 |
| 6,495,486 B1 | * | 12/2002 | Kamiya et al. | 502/209 |

FOREIGN PATENT DOCUMENTS

| | | |
|---|---|---|
| EP | 0 384 749 A1 | 8/1990 |
| EP | 0 794 151 A1 | 9/1997 |
| EP | 0 799 795 A2 | 10/1997 |

* cited by examiner

*Primary Examiner*—Wayne A. Langel
(74) *Attorney, Agent, or Firm*—Dickstein Shapiro Morin & Oshinsky, LLP

(57) ABSTRACT

Process for the preparation of a vanadium phosphate catalyst comprising treatment of a vanadium compound with formic acid, water and a phosphorus compound.

4 Claims, 1 Drawing Sheet

PROCESS FOR THE SYNTHESIS OF VPO CATALYSTS

This application claims the benefit of U.S. Provisional Application No. 60/171,455, filed Dec. 22, 1999.

BACKGROUND OF THE INVENTION

The present invention relates in general to catalytic oxidation of a hydrocarbon feed stock and in particular to preparation of a vanadyl hydrogen phosphate being a useful precursor of vanadium phosphate catalysts for the selective oxidation of hydrocarbons. Vanadium phosphates are important catalysts for the selective oxidation of hydrocarbons in particular in the selective oxidation of butane to maleic anhydride. One of the species showing high catalytic activity is vanadium pyrophosphate $((VO)_2P_2O_7)$, which is usually formed by a thermal transformation of $VOHPO_4.½H_2O$. Vanadyl phosphate can be prepared using known methods as disclosed in C. J. Hutchings, C. J. Kiely, M. T. Sananes-Schulz, yA. Burrows and J. C. Volta, Catalysis Today 40 (1998) 273. A first method (VPA) comprises of reduction of $V_2O_5$ with aqueous HCl followed by conversion with $H_3PO_4$ to give $VOHPO_4.½H_2O$. The second method (VPO) involves reduction of $V_2O_5$ with isobutanol in the presence of $H_3PO_4$. Another process (VPD) is related to a two-step procedure, in which $VOPO_4.2H_2O$ is prepared from $V_2O_5$ and $H_3PO_4$ in aqueous medium followed by a reduction of $VOPO_4.2H_2O$ to $VOHPO_4.½H_2O$ in isobutanol. The contemporary art involving aqueous methods involves not only HCl as reducing agent, but e.g. oxalic acid (DE Patent No. 19,645,066 A 1), $H_3PO_3$ (DD Patent No. 256, 659 A 1) and hydrazine (JP Patent No. 59,132,938) as well. The general object of this invention is to provide an improved catalyst for the catalytic oxidation of hydrocarbons and a method for the preparation of vanadyl hydrogenphosphate hemihydrate $(VOHPO_4.½H_2O)$, vanadyl hydrogenphosphate monohydrate $(β-VOHPO_4.H_2O)$ and trisvanadyl diphosphate pentahydrate $((VO)_3(PO_4)_2.5H_2O)$. $VOHPO_4.½H_2O$ prepared according the present invention is a useful precursor in the preparation of vanadium phosphate catalysts, while $β-VOHPO_4.H_2O$ and $(VO)_3(PO_4)_2.5H_2O$ require conversion to $VOHPO_4.½H_2O$ prior to catalysis. The precursors are prepared in formic acid/water mixtures being capable to reduce vanadium (V) to vanadium (IV). Generally, the use of formic acid in the preparation of a vanadium phosphate oxidation catalyst is known in the art as disclosed in e.g. U.S. Pat. No. 4,016,105. Here, the use of formic acid is described in combination with a secondary alcohol. A different system is disclosed in JP Patent No. 53,060,391 describing formic acid water mixtures containing Fe compounds, preferentially in combination with a carrier. Similarly, U.S. Pat. Nos. 4,388,221, 4,481,363, 4,562,269, 4,599,477, 4,639,530 and 4,801,567 describe reduction of V(V) with formic acid water mixtures containing Sn(II) with the aim of preparing supported catalysts for the oxidation of $C_4$ to $C_{10}$ hydrocarbons to maleic anhydride (U.S. Pat. Nos. 4,388,221, 4,481,363, 4,562,269, 4,639,530, 4,801,567) or supported catalysts for oxidative dehydrogenation of $C_4$ to $C_8$ mono-olefins (U.S. Pat. No. 4,599,477). A third preparation method (U.S. Pat. No. 4,179,404) involves formic acid in a less than stoichiometric amount in order to prevent 100% reduction of V(V) to V(IV). Another methodology is disclosed in EP Patent 71,140. The preparation of the catalyst precursor involves two steps: the synthesis of a vanadium (V) phosphate followed by reduction of V(V) to V(IV) using e.g. formic acid water mixtures affording a mixed vanadium phosphorus oxide. The description of prior art shows that there is an ongoing effort to develop oxidation catalysts by reduction of V(V) to V(IV) with organic and inorganic reducing agents. As a rule, the prior art has avoided the use of formic acid water mixtures, without any co-reducing agent in order to transform V(V) compounds in the presence of phosphorus compounds to crystalline vanadium (IV) phosphate hydrate compounds $((VO)_aH_b(PO_4)_c.dH_2O$; a=b=c=1, d=½; a=b=c=d=1; a=3, b=0, c=2, d=5). A further object of the invention relates to the application of these vanadium (IV) phosphate hydrate compounds as precursor to the oxidation of butane to maleic anhydride. The precursor is either used as prepared or, if applicable, converted to $VOHPO_4.½H_2O$.

SUMMARY OF THE INVENTION

Based on the above observation, this invention is a process for the preparation of a vanadium phosphate catalyst precursor for use in selective oxidation of a hydrocarbon feed stock comprising treatment of a vanadium compound with formic acid, water and a phosphorus compound.

DETAILED DESCRIPTION

Figure 1:
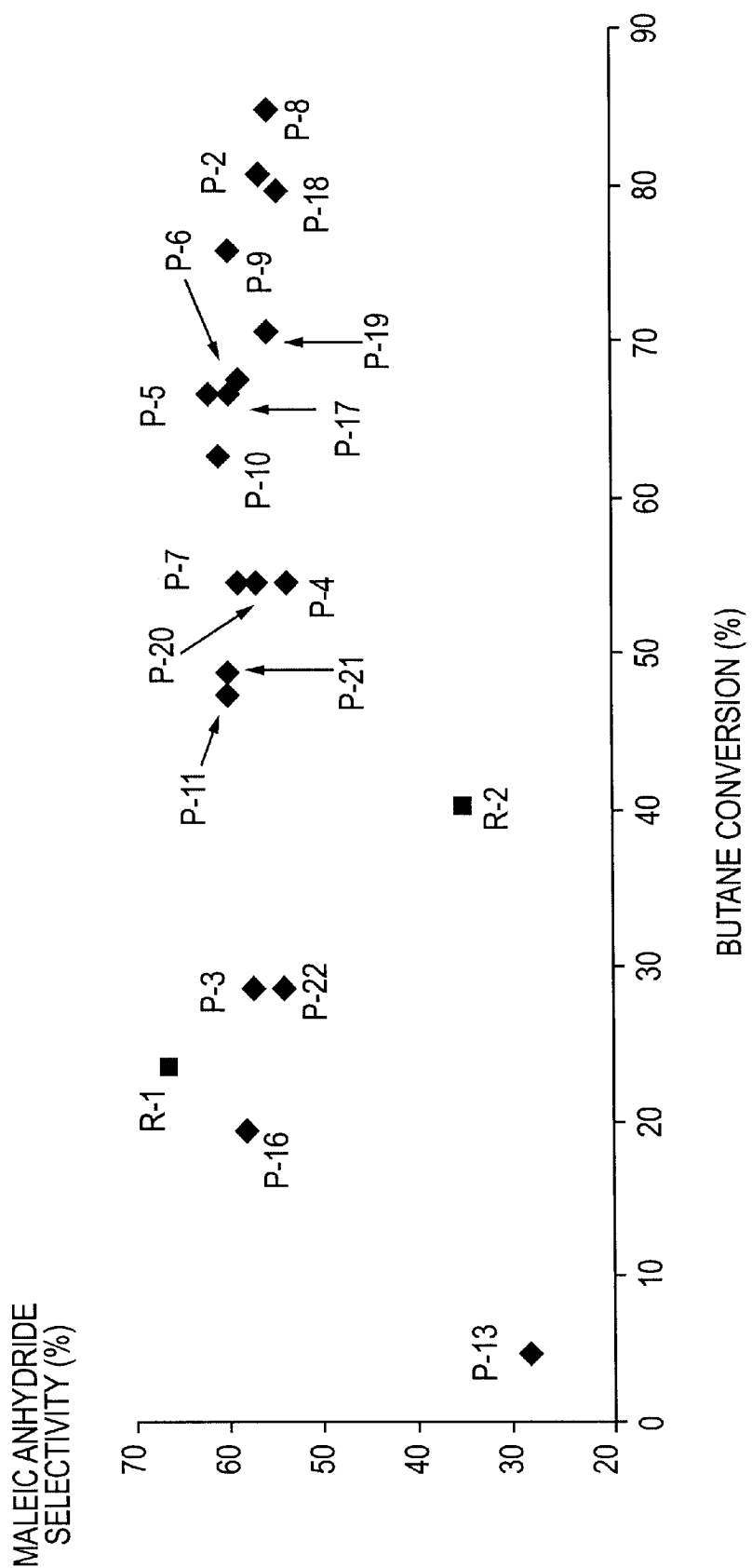
FIG. 1 presents an overview of catalytic activity of the different catalyst precursors.

Synthesis of $VOHPO_4.½H_2O$, $β-VOHPO_4.H_2O$ and $(VO)_3(PO_4)_2.5H_2O$ Precursors The invention is based on the observation that different products can be isolated from reaction mixtures containing a vanadium compound and a phosphorus compound in a formic acid-water solvent. Thus, the composition of the reaction mixture and the specific experimental procedure decisively influence the product formation. Suitable vanadium (V) compounds in these processes are $V_2O_5$, salts containing a $VO_3^-$ moiety such as $NH_4VO_3$ and salts containing a $VO^{3+}$ moiety such as $VOPO_4.2H_2O$. However, $V_2O_5$ is preferred. Relevant P(V) compounds are $H_3PO_4$ and $P_2O_5$. However, $H_3PO_4$ is preferred. Three main methods involving the preferred starting compounds can be distinguished:

Method A: A reaction mixture containing $V_2O_5$, $H_3PO_4$, HCOOH and $H_2O$ are heated to reflux for a specific period.

Method B: A reaction mixture containing $V_2O_5$, HCOOH and $H_2O$ are heated to reflux for a specific period; $H_3PO_4$ is added later.

Method C: A reaction mixture containing $V_2O_5$, HCOOH and $H_3PO_4$ are heated to reflux for a specific period; $H_2O$ is added later.

As a general experimental procedure using formic acid according to method A, the reagents are mixed at room temperature and subsequently heated under reflux for a period ranging from 20–170 h. The product is isolated by filtration washed with water and dried overnight at 110° C. An overview of preparations including two references is presented in Table 1. The references were prepared according to procedures known in the art i.e. using a mixture of isobutanol and benzylalcohol (R-1, cf. U.S. Pat. No. 4,132, 670) and using aqueous HCl (R-2, C. J. Kiely, A. Burrows, S. Sajip, G. J. Hutchings, M. T. Sananes, A. Tuel and J. C. Volta J. Catal. 162 (1996) 31).

Attached Table 1 shows complete reduction of V(V) to V(IV) in formic acid water mixtures having formic acid concentrations from 5% (P-15) to 91% (P-2, 3, 4). Incomplete reduction is observed in the absence of water (P-1) as apparent from the average oxidation state of vanadium (4.52). XRPD revealed the presence of VOHPO$_4$.½H$_2$O and (VO) (VO$_2$)$_2$H$_4$(PO$_4$)$_2$(P$_2$O$_7$)$_{0.5}$.xH$_2$O (0.01<x<2). The latter compound is known in the art (U.S. Pat. No. 4,374,756) and is claimed to be useful in the partial oxidation of hydrocarbons. The influence of water on the reduction of V$_2$O$_5$ can be rationalised assuming that the proteolysis equilibrium of H$_3$PO$_4$ and HCOOH is largely influenced by energetically favourable hydration of the protons by water (eq. 1 and 2). The increase in H$^+$ concentration favours the reduction of V$_2$O$_5$ as is evident from redox equation (3). Vanadium is present as VO$_2$$^+$ at a pH of around 2.0 (C. F. Tsang, J. Kim and A. Manthiram J. Mater. Chem. 8 (1998) 425).

$$H_3PO_4 + H_2O \rightleftharpoons H_3O^+ + H_2PO_4^- \qquad (1)$$

$$HCOOH + H_2O \rightleftharpoons H_3O^+ + HCOO^- \qquad (2)$$

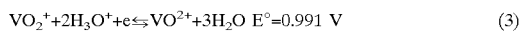

$$VO_2^+ + 2H_3O^+ + e \rightleftharpoons VO^{2+} + 3H_2O \quad E°=0.991 \text{ V} \qquad (3)$$

As apparent from Table 1, the composition of the reaction mixture not only affects the extent of reduction but the crystallisation of the vanadium phosphate product as well. Formation of VOHPO$_4$.½H$_2$O is observed in reaction mixtures containing 35% to 91% formic acid. The products were analysed with techniques, which are well known in the art i.e. XRPD, elemental analysis, Raman spectroscopy and BET. The P and V analyses of P-3, 5, 6, 10 showed reasonable agreement with the expected values of VOHPO$_4$.½H$_2$O. Based on XRPD the crystallite sizes (D$^{001}$) of VOHPO$_4$.½H$_2$O products were calculated and found to be larger than 300 Å. Raman spectroscopy revealed the presence of an unknown phase X in samples P-2, 5, 6 not observed by XRPD. This phase is probably responsible for the colour of the products, which was green-grey instead of the expected light blue colour. Product P-10 was pure VOHPO$_4$.½H$_2$O. The preparations in 91% formic acid involving methods A (P-2), B (P-3) and C (P-4) show that VOHPO$_4$.½H$_2$O is obtained regardless the specific procedure. It will be understood by those skilled in the art that for practical convenience only method A is preferred rather than method B and C. This does clearly neither limit nor exclude the utility of methods B and C in a large range of formic acid water mixtures. Furthermore, it will be understood by those skilled in the art that in method B complete reduction of V(V) to V(IV) precedes the reaction with H$_3$PO$_4$. To prove this, the product formed according to method B after complete reduction of V(V) to V(IV) in the absence of H$_3$PO$_4$ was isolated and extensively characterised. XRPD showed a pure phase characterized by a monoclinic unit cell (a=8.474 Å, b=8.385 Å, c=7.409 Å, β=90.44°) and space group P2$_1$/c. An overview of XRPD data is presented in attached Table 2.

Furthermore, elemental analysis clearly indicated the formation of VO(HCOO)$_2$.1½H$_2$O (calculated C 13.06%; H 2.74%; V 27.69%; found C 12.8%; H 2.84%; V 28.5%) which is known in the literature (Gmelins Handbuch der Anorganische Chemie, Vanadium Teil B, Springer Verlag, Weinheim 1967, page 345). Thus, it is obvious that method B is in fact equivalent to a process, in which a vanadium (IV) compound is reacted with H$_3$PO$_4$ in a specific formic acid water mixture. This conclusion is sustained by an experiment utilizing "VO$_2$" i.e. an oxide containing vanadium in an average oxidation state substantially lower than 5 (V$_7$O$_{13}$, V$_4$O$_9$, VO$_2$) instead of V$_2$O$_5$ (P-18, vide infra). The preparation of VOHPO$_4$.½H$_2$O is also possible in the presence of crystallisation reagents like H$_2$SO$_4$ (P-7), H$_3$CSO$_3$H (P-8) and p-toluene sulphonic acid (P-9). The use of these materials is well known in the art (G. U. Wolf, U. Rodemerck, A Brückner, M. Meisel and B. Kubias Catal. Lett. 46 (1997) 113) and has considerable influence on the catalytic activity (vide infra). Other products than VOHPO$_4$.½H$_2$O were observed in reaction mixtures containing 5–27% formic acid. In 27% formic acid (P-12) the crystallisation of the new compound (VO)$_3$(PO$_4$)$_2$.5H$_2$O was observed. This product was characterised by XRPD revealing a monoclinic cell with space group P2$_1$/c (a=19.77 Å, b=7.303 Å, c=9.226 Å, β=100.070°). An overview of XRPD data is listed in attached Table 3.

TGA (thermogravimetric analysis) of P-12 revealed a mass loss of 21.12% due to dehydration: 3.73% between 60° C. and 120° C. due to physisorbed water and 17.39% between 120° C. and 500° C. due to crystal water. This explains that the results on elemental analysis (Table 1) are in accordance with the composition (VO)$_3$(PO$_4$)$_2$.6H$_2$O (calc. V 30.63%, P 12.42%). However, TGA provides decisive evidence to assign the chemical composition of P-12 to the chemical formula (VO)$_3$(PO$_4$)$_2$.5H$_2$O. While the formation of (VO)$_3$(PO$_4$)$_2$.5H$_2$O is also observed in 5% formic acid (P-15), it has been found that the crystallisation process in 27% formic acid can be influenced by the addition of H$_2$SO$_4$ as crystallisation reagent. This procedure afforded the new compound β-VOHPO$_4$.H$_2$O (P-13), which is structurally clearly different from the VOHPO$_4$.H$_2$O modifications being described in the literature. Three types of VOHPO$_4$.H$_2$O are mentioned in the literature here designated α$_I$- (P. Amoros, R. Ibanez, E. Martinez-Tamayo, D. Beltran-Porter, A. Beltran-Porter Mater. Res. Bull. 24 (1989) 1347), α$_{II}$- (D. Beltran-Porter, A. Beltran-Porter, P. Amoros, R. Ibanez, E. Martinez, A. Le Bail, G. Ferey and G. Villeneuve, Eur. J. Solid St. Inorg. Chem. 28 (1991) 131) and α$_{III}$-VOHPO$_4$.H$_2$O (V. V. Gulliants, J. B. Benziger, S. Sundaresan, I. E. Wachs, J. M. Jehng and J. E. Roberts Catal. Today 28 (1996) 275). The lattice constants of the different systems including our modification is presented in attached Table 4, while attached Table 5 gives an overview of the XRPD data of P-13.

It will be understood by those skilled in the art that the XRPD analysis unambiguously demonstrates the structural diversity of the VOHPO$_4$.H$_2$O modifications mentioned in Table 4. Elemental analysis (calc. V 28.2%, P-17.1%, see Table 1) and TGA were used to determine the elemental composition of β-VOHPO$_4$.H$_2$O. TGA showed a weight loss of 14.82% in relation to dehydration, while 14.94% is expected for conversion of VOHPO$_4$.H$_2$O to (VO)$_2$P$_2$O$_7$. Thus, both TGA and elemental analysis unambiguously support the elemental composition of β-VOHPO$_4$.H$_2$O.

Apart from the preparations using V$_2$O$_5$ and H$_3$PO$_4$ other starting materials can be used as well. An overview of processes with alternative V and P starting materials is presented in attached Table 6.

Table 6 demonstrates the utility of alternative starting materials in preparation processes according to method A as outlined above. It has been shown that instead of V$_2$O$_5$, vanadium compounds like NH$_4$VO$_3$ (P-16), VOPO$_4$.2H$_2$O (P-17) and "VO2" (P-18) can be used for the preparation of VOHPO$_4$.½H$_2$O in formic acid water mixtures. It should be noted that the preparation involving NH$_4$VO$_3$ (P-16) required the addition of H$_2$SO$_4$ as crystallisation reagent. Furthermore, the preparation starting from VOPO$_4$.2H$_2$O (P-17) requires the addition of H$_3$PO$_4$ in order to avoid the undesired crystallisation of VO(HCOO)$_2$.1½H$_2$O. The preparation involving "VO2" (P-18) implies the use of vanadium oxides containing vanadium in an average oxidation state substantially lower than 5 and includes e.g. $V_7O_{13}$, $V_4O_9$ and $VO_2$. For brevity only, these oxides or mixtures thereof are designated "VO2". The preparation with $VO_2$ (P-18) demonstrates that successful use of formic acid water mixtures is not dependent on the degree of reduction occurring during the process. In relation to P compounds, it has been shown that $P_2O_5$ can be used instead of $H_3PO_4$ (P-19). This is as expected since $P_2O_5$ is converted to $H_3PO_4$ in reaction with water. The application of β-$VOHPO_4.H_2O$ as a precursor for the preparation of $VOHPO_4.½H_2O$ was initiated by the observation that direct application of β-$VOHPO_4.H_2O$ as a precursor for the selective oxidation of butane to maleic anhydride does not lead to an improvement of the state of the art (vide infra). Surprisingly, it has been found that β-$VOHPO_4.H_2O$ (P-13) can be transformed to $VOHPO_4.½H_2O$ (P-20) by means of a recrystallisation process in acetic acid. Thus, a new precursor P-20 is formed from β-$VOHPO_4.H_2O$ (P-13) showing interesting catalytic properties (vide infra). It is another object of this invention that the recrystallisation principle could not only be applied to β-$VOHPO_4.H_2O$ but to $(VO)_3(PO_4)_2.5H_2O$ (P-12, P-14, P-15) as well. It is well known in the art that the best industrial vanadium phosphate catalysts contain a P/V atomic ratio slightly higher than unity (D. Wang, M. C. Kung and H. H. Kung Catal. Lett. 65 (2000) 9). Investigations involving precursors with a P/V ratio <1 show that both the butane conversion and selectivity to maleic anhydride formation are negatively influenced (N. Yamazoe, H. Morishige and Y. Teraoka, Stud. Surf. Sci. Catal. 44 (1988) 15). Thus, $(VO)_3(PO_4)_2.5H_2O$ is an unfavourable catalyst precursor with a P/V atomic ratio of 0.67. In this respect, the conversion of $(VO)_3(PO_4)_2.5H_2O$ with of $H_3PO_4$ to $VOHPO_4.½H_2O$ in acetic acid (P-21) is highly interesting. Moreover, it has been shown that the transformation of $(VO)_3(PO_4)_2.5H_2O$ to $VOHPO_4.½H_2O$ can also be accomplished using 60% formic acid (P-22). Thus, interesting catalyst precursors can be obtained in formic acid water mixtures containing 91–5% formic acid, if applicable in combination with a recrystallisation procedure.

In summary, we have demonstrated the successful preparation of $VOHPO_4.½H_2O$ or β-$VOHPO_4.H_2O$ or $(VO)_3(PO_4)_2.5H_2O$ using:

1) method A, B, C;
2) formic acid/water mixtures with a formic acid content of 91–5%;
3) $V_2O_5$, $NH_4VO_3$, $VO_2$ and $VOPO_4.2H_2O$ as vanadium precursors;
4) $H_3PO_4$ and $P_2O_5$ as phosphorus precursors;
5) recrystallisation of β-$VOHPO_4.H_2O$ (using acetic acid) and $(VO)_3(PO_4)_2.5H_2O$ (using acetic acid or a formic acid-water mixture).

Catalytic Activity of $VOHPO_4.½H_2O$, β-$VOHPO_4.H_2O$ or $(VO)_3 (PO_4)_2.5H_2O$ Precursors The catalytic activity of $VOHPO_4.½H_2O$ or β-$VOHPO_4.H_2O$ precursors was evaluated in relation to the selective oxidation of butane. The precursors were pressed to pellets after which a sieve fraction 0.3–0.7 mm was prepared. This material was activated in accordance with the general principles disclosed in U.S. Pat. No. 4,132,670 i.e. oxidative calcination in air followed by equilibration in the gas feed.

The activation details are the following:
heating in air for 1 h at a given temperature; gas shift to 1.29% n-butane in synthetic air with a flow of 100 ml.min$^{-1}$g$^{-1}$;
heating up to a given equilibration temperature for 17 h; cooling to 400° C. and measuring the catalytic activity under WHSV 6000 h$^{-1}$.

An overview of catalytic activity of the different precursors including the references is presented in attached Table 7 and in attached FIG. 1.

FIG. 1 and Table 7 demonstrate clearly the improved catalytic activity of most precursors derived from the formic acid process in comparison with R-1 (a state of the art alcoholic catalyst) and R-2 (a state of the art aqueous catalyst). The low activity of P-13 indicates that β-$VOHPO_4.H_2O$ cannot be used as a catalyst precursor. P-3, P-16 and P-22 show low activity, which is still comparable to R-1 and clearly better than R-2. It is, therefore, obvious that the preparation procedures according to P-3, P-16 and P-22 are less preferred. Generally, a maleic anhydride selectivity of approximately 60% is observed with formic acid precursors, which is slightly less than R-1. However, the high selectivity is maintained at conversion levels between 47% and 84%. This is the crucial property of formic acid precursors, which is evident from 14 precursors shown in Table 7 and FIG. 1. Thus, a large range of procedures can be used for the preparation of a precursor being substantially more active in comparison with the state of the art references.

EXAMPLES

Example 1

Method A, General Procedure: Synthesis of P-2

A suspension of $V_2O_5$ (9.10 g) in a mixture of formic acid (250 mL), $H_3PO_4$ (7.5 mL) and water (25 mL) is heated to reflux for 44 h. Then, the green-grey suspension is cooled to room temperature and filtered. The greenish grey solid is washed with water and dried at 110° C. for 16 h.

Example 2

Method B: Synthesis of P-3

A suspension of $V_2O_5$ (3.64 g) in a mixture of formic acid (100 mL) and water (10 mL) is heated to reflux for 72 h. Then, $H_3PO_4$ (mL) is added to the dark green suspension and reflux is continued for 24 h. Then the blue suspension is cooled to room temperature and filtered. The blue solid is washed with water and dried at 110° C. for 16 h.

Example 3

Method C: Synthesis of P-4

A suspension of $V_2O_5$ (1.82 g) in a mixture of formic acid (50 mL) and $H_3PO_4$ (1.5 mL) is heated to reflux for 144 h. Then $H_2O$ (5 mL) is added to the green suspension and reflux is continued for 20 h. Then, the blue suspension is cooled to room temperature and filtered. The blue solid is washed with water and dried at 110° C. for 16 h.

Example 4

Conversion of β-$VOHPO_4.H_2O$ (P-13) to $VOHPO_4.½H_2O$ (P-20). A suspension of β-$VOHPO_4.H_2O$ (11.60 g) in acetic acid (400 mL) is heated under reflux for 20 h. The light green suspension is cooled to room temperature and filtered. The light greenish grey solid is washed with water and dried at 110° C. for 16 h.

Example 5

Conversion of $(VO)_3(PO_4)_2.5H_2O$ (P 12) to $VOHPO_4.½H_2O$ (P-22) A suspension of $(VO)_3(PO_4)_2.5H_2O$ (3.21 g) in a mixture of $H_3PO_4$ (590 μl) and 60% formic acid (100 mL) is heated under reflux for 20 h. The light blue suspension is cooled to room temperature and filtered. The blue solid is washed with water and dried at 110° C. for 16 h.

While the character of this invention has been described with numerous examples, this has been done by way of illustration only and without limitation of the invention. It will be apparent to those skilled in the art that certain features of the invention may be altered, while staying within the basic spirit of the invention which is more explicitly defined by the following claims.

TABLE 1

Overview of preparations (P) involving V2O5/H3PO4/formic acid/water reaction mixtures including state of the art references (R).

| Precursor | Method | Formic acid (%) | Time (h) | color product | XRPD phase | D (001) (Å) | BET m2.g-1 | V (%)1 | Average Ox. State V | P (%)1 |
|---|---|---|---|---|---|---|---|---|---|---|
| P-1 | A | 100 | 96 | light green | VOHPO4.½H2O2 | 649 | 5 | 26.50 | 4.52 | 16.20 |
| P-2 | A | 91 | 44 | green-grey | VOHPO4.½H2O | 528 | 14 | — | 4.01 | — |
| P-3 | B | 91 | 96 | light blue | VOHPO4.½H2O | >1000 | 5 | 28.70 | 4.01 | 18.80 |
| P-4 | C | 91 | 164 | light blue | VOHPO4.½H2O | 890 | 5 | — | — | — |
| P-5 | A | 82 | 44 | green-grey | VOHPO4.½H2O | 553 | 14 | 28.70 | 4.02 | 17.10 |
| P-6 | A | 60 | 44 | green-grey | VOHPO4.½H2O | 891 | — | 29.10 | 4.03 | 17.10 |
| P-73 | A | 60 | 7 | light blue | VOHPO4.½H2O | 559 | 8 | — | — | — |
| P-83 | A | 60 | 7 | green-grey | VOHPO4.½H2O | >1000 | 11 | — | — | — |
| P-93 | A | 60 | 7 | green-grey | VOHPO4.½H2O | 625 | 8 | — | — | — |
| P-10 | A | 44 | 20 | light blue | VOHPO4.½H2O | 383 | 14 | 28.30 | 4.01 | 17.10 |
| P-11 | A | 35 | 44 | light blue | VOHPO4.½H2O | 815 | — | — | — | — |
| P-12 | A | 27 | 65 | light blue | (VO)3(PO4)2.5H2O4 | — | 12 | 29.40 | — | 12.40 |
| P-13 | A | 27 | 144 | light blue | β-VOHPO4.H2O5 | — | 5 | 27.60 | 4.01 | 17.10 |
| P-14 | A | 9 | 44 | light blue | (VO)3(PO4)2.5H2O | — | 7 | 29.30 | 3.96 | 12.20 |
| P-15 | A | 5 | 96 | light blue | (VO)3(PO4)2.5H2O | — | — | 30.10 | 4.01 | 12.90 |
| R-16 | — | — | 24 | light blue | VOHPO4.½H2O | 109 | 33 | 28.10 | 4.01 | 18.00 |
| R-27 | — | — | 3 | green | VOHPO4.½H2O | >1000 | 1 | — | — | — |

1VOHPO4.½H2O requires P 18.1%; V: 29.7%.
2(VO)(VO2)2H4(PO4)2(P2O7)0.5.xH2O is present as well.
3Reaction in the presence of crystallization reagents (see text).
4A new compound (see text).
5A new compound, obtained in the presence of crystallization reagents (see text).
6prepared in a mixture of benzylalcohol and isobutanol (U.S. Pat. No. 4,132,670).
7Prepared in aqueous HCl according to J. Catal. 162 (1996) 31.

TABLE 2

XRPD data of VO(HCOO)₂.1½H₂O.

| h | k | l | Calculated d-spacing [Å] | Observed d-spacing [Å] | Difference in d-spacing [Å] | Relative intensity |
|---|---|---|---|---|---|---|
| 1 | 1 | −1 | 4.649 | 4.656 | −0.007 | 100 |
| 2 | 0 | 0 | 4.234 | 4.237 | −0.004 | 7 |
| 2 | 1 | 0 | 3.780 | 3.782 | −0.002 | 2 |
| 0 | 0 | 2 | 3.706 | 3.704 | 0.002 | 55 |
| 1 | 2 | −1 | 3.356 | 3.356 | −0.000 | 13 |
| 1 | 1 | −2 | 3.154 | 3.153 | 0.001 | 9 |
| 2 | 2 | 0 | 2.982 | 2.980 | 0.002 | 20 |
| 2 | 0 | 2 | 2.778 | 2.779 | −0.001 | 4 |
| 1 | 3 | 0 | 2.653 | 2.654 | −0.002 | 9 |
| 3 | 1 | 1 | 2.510 | 2.512 | −0.002 | 3 |
| 1 | 3 | 1 | 2.499 | 2.497 | 0.002 | 2 |
| 2 | 3 | 0 | 2.333 | 2.333 | −0.000 | 10 |
| 1 | 1 | −3 | 2.285 | 2.285 | −0.001 | 18 |
| 3 | 2 | −1 | 2.237 | 2.238 | −0.000 | 6 |
| 1 | 3 | −2 | 2.161 | 2.160 | 0.001 | 3 |
| 0 | 4 | 0 | 2.098 | 2.096 | 0.001 | 7 |
| 1 | 2 | 3 | 2.059 | 2.061 | −0.002 | 16 |
| 2 | 3 | −2 | 1.978 | 1.978 | 0.001 | 8 |
| 1 | 4 | −1 | 1.964 | 1.963 | 0.001 | 3 |
| 3 | 3 | −1 | 1.921 | 1.921 | −0.000 | 6 |
| 2 | 2 | 3 | 1.895 | 1.897 | −0.002 | 4 |
| 2 | 4 | 0 | 1.880 | 1.879 | 0.001 | 6 |
| 0 | 0 | 4 | 1.855 | 1.852 | 0.003 | 21 |
| 2 | 4 | 1 | 1.816 | 1.820 | −0.004 | 33 |
| 2 | 3 | −3 | 1.699 | 1.699 | −0.000 | 9 |
| 5 | 1 | −1 | 1.625 | 1.624 | 0.001 | 5 |
| 1 | 5 | −1 | 1.607 | 1.606 | 0.001 | 6 |
| 2 | 2 | −4 | 1.576 | 1.577 | −0.001 | 10 |
| 3 | 3 | −3 | 1.550 | 1.552 | −0.002 | 13 |
| 2 | 4 | 3 | 1.493 | 1.493 | −0.000 | 3 |
| 1 | 1 | −5 | 1.440 | 1.440 | 0.001 | 9 |
| 3 | 5 | −1 | 1.417 | 1.416 | −0.000 | 4 |

TABLE 3

XRPD data of (VO)₃(PO4)₂.5H₂O (P-12).

| h | k | l | Calculated d-spacing [Å] | Observed d-spacing [Å] | Difference in d-spacing [Å] | Relative intensity |
|---|---|---|---|---|---|---|
| 2 | 0 | 0 | 9.734 | 9.694 | 0.039 | 100 |
| 1 | 1 | 0 | 6.837 | 6.818 | 0.020 | 30 |
| 1 | 1 | −1 | 5.631 | 5.610 | 0.022 | 11 |
| 1 | 1 | 1 | 5.308 | 5.295 | 0.013 | 8 |
| 4 | 0 | 0 | 4.867 | 4.860 | 0.007 | 33 |

TABLE 3-continued

XRPD data of (VO)$_3$(PO$_4$)$_2$·5H$_2$O (P-12).

| h | k | l | Calculated d-spacing [Å] | Observed d-spacing [Å] | Difference in d-spacing [Å] | Relative intensity |
|---|---|---|---|---|---|---|
| 2 | 0 | −2 | 4.423 | 4.416 | 0.006 | 29 |
| 3 | 1 | 1 | 4.064 | 4.062 | 0.002 | 5 |
| 4 | 1 | 0 | 4.050 | 4.046 | 0.004 | 3 |
| 5 | 0 | 0 | 3.893 | 3.886 | 0.007 | 19 |
| 2 | 0 | 2 | 3.865 | 3.864 | 0.001 | 11 |
| 1 | 1 | 2 | 3.680 | 3.676 | 0.004 | 12 |
| 0 | 2 | 0 | 3.651 | 3.650 | 0.001 | 9 |
| 5 | 1 | 0 | 3.436 | 3.431 | 0.004 | 9 |
| 1 | 2 | −1 | 3.375 | 3.378 | −0.003 | 27 |
| 6 | 0 | 0 | 3.245 | 3.245 | −0.001 | 3 |
| 2 | 2 | 1 | 3.137 | 3.128 | 0.009 | 29 |
| 5 | 1 | 1 | 3.061 | 3.062 | −0.001 | 24 |
| 6 | 0 | −2 | 2.890 | 2.886 | 0.004 | 31 |
| 1 | 1 | −3 | 2.834 | 2.832 | 0.002 | 5 |
| 4 | 2 | 1 | 2.699 | 2.701 | −0.002 | 3 |
| 7 | 1 | 0 | 2.599 | 2.597 | 0.002 | 5 |
| 2 | 1 | 3 | 2.580 | 2.578 | 0.002 | 3 |
| 5 | 1 | 2 | 2.557 | 2.555 | 0.001 | 2 |
| 6 | 2 | −1 | 2.424 | 2.422 | 0.002 | 7 |
| 2 | 2 | −3 | 2.339 | 2.343 | −0.004 | 4 |
| 6 | 1 | 2 | 2.319 | 2.319 | 0.000 | 8 |
| 0 | 0 | 4 | 2.271 | 2.271 | 0.000 | 4 |
| 2 | 1 | −4 | 2.196 | 2.195 | 0.001 | 4 |
| 4 | 3 | 0 | 2.177 | 2.177 | 0.000 | 3 |
| 0 | 1 | 4 | 2.168 | 2.172 | −0.004 | 3 |
| 5 | 2 | −3 | 2.130 | 2.129 | 0.001 | 2 |
| 1 | 3 | 2 | 2.114 | 2.114 | 0.000 | 2 |
| 2 | 3 | 2 | 2.060 | 2.060 | 0.000 | 3 |
| 3 | 0 | 4 | 2.035 | 2.036 | 0.000 | 2 |
| 8 | 2 | 0 | 2.025 | 2.024 | 0.001 | 2 |
| 9 | 1 | −2 | 2.019 | 2.018 | 0.000 | 2 |
| 4 | 2 | 3 | 2.000 | 1.998 | 0.002 | 3 |
| 3 | 3 | 2 | 1.989 | 1.987 | 0.002 | 2 |
| 6 | 1 | −4 | 1.960 | 1.960 | 0.001 | 2 |
| 8 | 2 | −2 | 1.958 | 1.957 | 0.002 | 2 |
| 9 | 1 | 1 | 1.952 | 1.954 | −0.001 | 3 |
| 5 | 3 | −2 | 1.948 | 1.950 | −0.002 | 2 |
| 10 | 0 | 0 | 1.947 | 1.947 | 0.000 | 3 |
| 8 | 1 | 2 | 1.933 | 1.933 | −0.001 | 2 |
| 10 | 0 | −2 | 1.915 | 1.914 | 0.000 | 3 |
| 7 | 1 | −4 | 1.868 | 1.867 | 0.001 | 1 |
| 0 | 4 | 0 | 1.826 | 1.826 | −0.001 | 3 |
| 1 | 4 | 0 | 1.818 | 1.819 | −0.001 | 3 |
| 5 | 3 | 2 | 1.817 | 1.816 | 0.001 | 3 |
| 8 | 2 | −3 | 1.809 | 1.809 | 0.000 | 3 |
| 0 | 4 | 1 | 1.790 | 1.790 | −0.001 | 3 |
| 2 | 1 | −5 | 1.789 | 1.789 | 0.000 | 5 |
| 1 | 4 | −1 | 1.788 | 1.788 | 0.000 | 3 |
| 6 | 2 | 3 | 1.783 | 1.782 | 0.001 | 3 |
| 4 | 1 | −5 | 1.756 | 1.756 | 0.000 | 1 |
| 11 | 1 | −1 | 1.745 | 1.745 | 0.000 | 3 |
| 10 | 1 | −3 | 1.735 | 1.736 | −0.001 | 2 |
| 10 | 2 | 0 | 1.718 | 1.718 | 0.000 | 2 |
| 4 | 3 | 3 | 1.706 | 1.706 | 0.000 | 1 |
| 0 | 4 | −2 | 1.694 | 1.695 | −0.001 | 1 |
| 2 | 4 | −2 | 1.688 | 1.687 | 0.000 | 1 |
| 3 | 3 | −4 | 1.660 | 1.659 | 0.001 | 1 |
| 2 | 2 | −5 | 1.647 | 1.646 | 0.000 | 1 |
| 12 | 0 | 0 | 1.622 | 1.623 | −0.001 | 3 |
| 7 | 1 | 4 | 1.586 | 1.587 | −0.001 | 1 |
| 8 | 2 | 3 | 1.580 | 1.580 | 0.000 | 1 |
| 6 | 3 | 3 | 1.565 | 1.565 | 0.000 | 5 |
| 4 | 2 | 5 | 1.475 | 1.475 | 0.000 | 1 |
| 6 | 4 | −3 | 1.461 | 1.461 | 0.000 | 1 |
| 2 | 5 | 0 | 1.444 | 1.444 | 0.000 | 1 |
| 2 | 1 | 6 | 1.430 | 1.430 | 0.000 | 1 |
| 11 | 1 | −5 | 1.371 | 1.371 | 0.000 | 1 |

TABLE 4

Overview of cell parameters of VOHPO$_4$·H$_2$O modifications.

| Name | Space group | a [Å] | b [Å] | c [Å] | β [°] | V [Å$^3$] |
|---|---|---|---|---|---|---|
| α$_I$-VOHPO$_4$·H$_2$O | P2$_1$/c | 6.546 | 7.37 | 9.44 | 95.11 | 453.6 |
| α$_{II}$-VOHPO$_4$·H$_2$O | P2$_1$/c | 6.92 | 7.26 | 9.32 | 70.91 | 442.5 |
| α$_{III}$-VOHPO$_4$·H$_2$O | Orthorhombic | 7.22 | 6.48 | 5.61 | 90 | 262.8 |
| β-VOHPO$_4$·H$_2$O (P-13) | P2$_1$/c | 6.90 | 7.36 | 9.27 | 104.8 | 455.3 |

TABLE 5

XRPD data of β-VOHPO$_4$·H$_2$O (P-13).

| h | k | l | Calculated d-spacing [Å] | Observed d-spacing [Å] | Difference in d-spacing [Å] | Relative intensity |
|---|---|---|---|---|---|---|
| 1 | 0 | 0 | 6.677 | 6.687 | −0.010 | 100 |
| 0 | 1 | −1 | 5.689 | 5.687 | 0.002 | 16 |
| 1 | 1 | 0 | 4.946 | 4.950 | −0.004 | 10 |
| 0 | 0 | 2 | 4.479 | 4.480 | −0.001 | 11 |
| 1 | 0 | −2 | 4.257 | 4.258 | −0.001 | 4 |
| 1 | 1 | 1 | 4.020 | 4.018 | 0.002 | 6 |
| 0 | 1 | 2 | 3.827 | 3.827 | −0.001 | 15 |
| 1 | 1 | −2 | 3.685 | 3.684 | 0.001 | 2 |
| 0 | 2 | 1 | 3.406 | 3.405 | 0.001 | 9 |
| 1 | 0 | 2 | 3.345 | 3.346 | −0.001 | 64 |
| 1 | 2 | 0 | 3.224 | 3.224 | 0.001 | 2 |
| 1 | 2 | −1 | 3.161 | 3.159 | 0.002 | 36 |
| 2 | 1 | −1 | 3.108 | 3.105 | 0.003 | 14 |
| 2 | 0 | −2 | 3.080 | 3.080 | 0.000 | 25 |
| 2 | 1 | −2 | 2.842 | 2.841 | 0.001 | 6 |
| 1 | 1 | −3 | 2.802 | 2.801 | 0.001 | 15 |
| 2 | 1 | 1 | 2.695 | 2.693 | 0.002 | 3 |
| 1 | 2 | 2 | 2.476 | 2.476 | 0.000 | 2 |
| 2 | 1 | −3 | 2.432 | 2.432 | 0.000 | 3 |
| 2 | 0 | 2 | 2.399 | 2.400 | −0.001 | 55 |
| 2 | 2 | −2 | 2.363 | 2.364 | −0.001 | 3 |
| 1 | 0 | −4 | 2.309 | 2.309 | 0.000 | 4 |
| 1 | 3 | −1 | 2.280 | 2.279 | 0.001 | 6 |
| 3 | 0 | −2 | 2.234 | 2.233 | 0.001 | 5 |
| 3 | 1 | −1 | 2.197 | 2.198 | −0.001 | 5 |
| 2 | 0 | −4 | 2.128 | 2.129 | 0.000 | 8 |
| 2 | 2 | −3 | 2.111 | 2.112 | −0.001 | 4 |
| 1 | 2 | 3 | 2.067 | 2.068 | 0.000 | 4 |
| 2 | 1 | −4 | 2.045 | 2.046 | −0.001 | 5 |
| 2 | 2 | 2 | 2.010 | 2.010 | 0.000 | 3 |
| 2 | 3 | 0 | 1.978 | 1.977 | 0.001 | 4 |
| 3 | 2 | −1 | 1.952 | 1.953 | −0.001 | 4 |
| 1 | 3 | −3 | 1.907 | 1.908 | 0.000 | 5 |
| 0 | 4 | 0 | 1.841 | 1.842 | −0.001 | 4 |
| 3 | 0 | −4 | 1.830 | 1.829 | 0.000 | 5 |
| 3 | 0 | 2 | 1.817 | 1.818 | −0.001 | 5 |
| 3 | 2 | −3 | 1.793 | 1.793 | 0.000 | 7 |
| 3 | 2 | 1 | 1.785 | 1.785 | 0.000 | 6 |
| 1 | 4 | −1 | 1.764 | 1.764 | 0.000 | 5 |
| 2 | 2 | 3 | 1.749 | 1.748 | 0.001 | 4 |
| 1 | 2 | 4 | 1.741 | 1.742 | 0.000 | 4 |
| 4 | 0 | −2 | 1.714 | 1.714 | 0.000 | 11 |
| 1 | 4 | −2 | 1.690 | 1.690 | 0.000 | 5 |
| 4 | 0 | 0 | 1.669 | 1.669 | 0.000 | 15 |
| 3 | 3 | −2 | 1.652 | 1.652 | 0.000 | 5 |
| 2 | 3 | −4 | 1.608 | 1.608 | 0.000 | 8 |
| 2 | 2 | −5 | 1.602 | 1.603 | −0.001 | 2 |
| 2 | 4 | −2 | 1.580 | 1.580 | 0.000 | 6 |
| 1 | 0 | −6 | 1.543 | 1.543 | 0.000 | 3 |
| 4 | 1 | 1 | 1.536 | 1.536 | 0.000 | 7 |
| 4 | 2 | 0 | 1.520 | 1.520 | 0.000 | 4 |
| 1 | 1 | −6 | 1.511 | 1.510 | 0.001 | 3 |
| 4 | 2 | −3 | 1.504 | 1.503 | 0.000 | 3 |
| 0 | 0 | 6 | 1.493 | 1.492 | 0.001 | 12 |
| 3 | 2 | −5 | 1.476 | 1.476 | 0.000 | 2 |
| 0 | 1 | 6 | 1.463 | 1.463 | 0.001 | 4 |
| 1 | 4 | −4 | 1.439 | 1.440 | 0.000 | 6 |

TABLE 5-continued

XRPD data of β-VOHPO$_4$.H$_2$O (P-13).

| h | k | l | Calculated d-spacing [Å] | Observed d-spacing [Å] | Difference in d-spacing [Å] | Relative intensity |
|---|---|---|---|---|---|---|
| 3 | 0 | -6 | 1.419 | 1.419 | 0.000 | 6 |
| 3 | 0 | 4 | 1.409 | 1.409 | 0.000 | 6 |
| 2 | 1 | 5 | 1.407 | 1.407 | 0.000 | 3 |
| 5 | 0 | -2 | 1.380 | 1.380 | 0.000 | 9 |
| 1 | 5 | 2 | 1.348 | 1.348 | 0.000 | 5 |

TABLE 6

Overview of preparations according to method A using alternative starting materials

| Precursor | V compound | P compound | Formic acid (%) | Time (h) | color product | XRPD phase | D (001) (Å) | BET m2.g-1 |
|---|---|---|---|---|---|---|---|---|
| P-16 | NH4VO3 | H3PO4 | 60 | 72 | light blue | VOHPO4.½H2O1 | >1000 | 3.8 |
| P-17 | VOPO4.2H2O | H3PO42 | 60 | 7 | green-grey | VOHPO4.½H2O | 640 | 6.3 |
| P-18 | VO2 | H3PO4 | 82 | 17 | green-grey | VOHPO4.½H2O | 734 | 8.9 |
| P-19 | V2O5 | P2O5 | 60 | 18 | green-grey | VOHPO4.½H2O | >1000 | 7.6 |
| P-20 | β-ζOHΠO4.H2O | — | pure3 | 18 | light blue | VOHPO4.½H2O | 190 | 14.8 |
| P-21 | (VO)3(PO4)2.5H2O | H3PO4 | pure3 | 20 | light green | VOHPO4.½H2O | 350 | — |
| P-22 | (VO)3(PO4)2.5H2O | H3PO4 | 60 | 20 | light blue | VOHPO4.½H2O | >1000 | — |

1Obtained in the presence of H2SO4.
210 mol % in relation to VOPO4.
3Recrystallization process in acetic acid.

TABLE 7

Catalystic activity1 of formic acid catalyst (P) in comparision with state of the art systems (R).

| Precursor | Calcination (° C.) | Equilibration (° C.) | Butane conversion (%) | Maleic anhydride selectivity (%) | Maleic anhydride yield (%) |
|---|---|---|---|---|---|
| P-2 | 350 | 420 | 80 | 58 | 47 |
| P-3 | 370 | 420 | 28 | 58 | 16 |
| P-4 | 350 | 420 | 54 | 55 | 30 |
| P-5 | 350 | 420 | 66 | 63 | 42 |
| P-6 | 350 | 420 | 67 | 60 | 41 |
| P-7 | 350 | 420 | 54 | 60 | 32 |
| P-8 | 350 | 420 | 84 | 57 | 48 |
| P-9 | 350 | 420 | 75 | 61 | 46 |
| P-10 | 360 | 420 | 62 | 62 | 39 |
| P-11 | 360 | 420 | 47 | 61 | 29 |
| P-13 | 350 | 420 | 5 | 29 | 1 |
| P-16 | 350 | 420 | 19 | 59 | 11 |
| P-17 | 350 | 420 | 66 | 61 | 40 |
| P-18 | 350 | 420 | 79 | 56 | 44 |
| P-19 | 350 | 420 | 70 | 57 | 40 |
| P-20 | 350 | 420 | 54 | 58 | 31 |
| P-21 | 350 | 420 | 48 | 61 | 29 |
| P-22 | 350 | 420 | 28 | 55 | 15 |
| R-1 | 390 | 460 | 23 | 67 | 16 |
| R-2 | 365 | 420 | 40 | 36 | 14 |

1Measured at 400° C. with WHSV 6000 h-1 after calcination in air for 1 h and equilibration in a mixture of butane (1.29%), oxygen (19.69%) and nitrogen (79.02%) for 17 h.

What is claimed is:

1. A process for the preparation of VOHPO$_4$.½H$_2$O by treatment of (VO)$_3$(PO$_4$)$_2$.5H$_2$O with the following structural properties: space group $P2_{1/c}$ (a=19.77 Å, b=7.303 Å, c=9.226 Å, β=100.07°, V=1311.5 Å$^3$) or β-VOHPO$_4$.H$_2$O with the following structural properties: space group $P2_{1/c}$ (a=6.90 Å, b=7.36 Å, c=9.27 Å; β=104.8°; V=455.3 Å$^3$) with dilute formic acid and/or acetic acid.

2. A process for the preparation of a catalyst comprising the steps of preparing VOHPO$_4$.½H$_2$O by treatment of (VO)$_3$(PO$_4$)$_2$.5H$_2$O with the following structural properties: space group $P2_{1/c}$ (a=19.77 Å, b=7.303 Å, c=9.226 Å, β=100.07°, V=1311.5 Å$^3$) or β-VOHPO$_4$.H$_2$O with the following structural properties: space group $P2_{1/c}$ (a=6.90 Å, b=7.36 Å, c=9.27 Å, β=104.8°, V=455.3 Å$^3$) with dilute formic acid and/or acetic acid, followed by calcining the VOHPO$_4$.½H$_2$O at temperatures ranging from 300° C. to 500° C. in air.

3. A vanadium phosphate compound β-VOHPO$_4$.H$_2$O being characterized by the following structural data: space group $P2_{1/c}$ (a=6.90 Å, b=7.36 Å, c=9.27 Å, β=104.8°, V=455.4 Å$^3$).

4. A vanadium phosphate compound (VO)$_3$(PO$_4$)$_2$.5H$_2$O being characterized by the following structural data: space group $P2_{1/c}$ (a=19.77 Å, b=7.303 Å, c=9.226 Å, β=100.07°, V=1311.5 Å$^3$).

* * * * *